United States Patent
Andrä

(10) Patent No.: US 6,168,780 B1
(45) Date of Patent: Jan. 2, 2001

(54) MARKER FOR DETERMINING ITS POSITION IN A CAVITY INSIDE THE ORGANISM OF A LIVING BEING

(75) Inventor: Wilfried Andrä, Jena (DE)

(73) Assignees: Institut fuer Physikalische Hochtechnologie e.V.; Aesculap Meditec GmbH, both of Jena (DE)

( * ) Notice: Under 35 U.S.C. 154(b), the term of this patent shall be extended for 0 days.

(21) Appl. No.: 09/355,814

(22) PCT Filed: Feb. 19, 1998

(86) PCT No.: PCT/EP98/00940

§ 371 Date: Aug. 4, 1999

§ 102(e) Date: Aug. 4, 1999

(87) PCT Pub. No.: WO98/37826

PCT Pub. Date: Sep. 3, 1998

(30) Foreign Application Priority Data

Feb. 26, 1997 (DE) ............................................. 197 07 556

(51) Int. Cl.[7] .................................................. A61B 5/055
(52) U.S. Cl. ...................... 424/9.32; 424/9.322; 424/9.3; 128/899
(58) Field of Search ................................ 424/9.32, 9.322, 424/9.3, 455; 600/420; 128/899

(56) References Cited

U.S. PATENT DOCUMENTS

| | | | |
|---|---|---|---|
| 4,735,796 | * | 4/1988 | Gordon ................................ 424/9.32 |
| 4,996,991 | * | 3/1991 | Gordon ................................ 424/9.32 |
| 5,314,681 | * | 5/1994 | Leunbach et al. .................. 424/9.32 |
| 5,676,927 | * | 10/1997 | Nakagami et al. ................. 424/9.32 |
| 5,735,279 | * | 4/1998 | Klaveness et al. .................. 600/409 |
| 6,048,515 | * | 4/2000 | Kresse et al. ...................... 424/9.322 |
| 6,082,366 | * | 7/2000 | Andra et al. ......................... 128/899 |

FOREIGN PATENT DOCUMENTS

WO97/09640    3/1997    (WO) .

OTHER PUBLICATIONS

M. Reiser, W. Semmler (Hrsg) "Magnetresonanztomographie", Springer–Verlag, Berlin/Heidelberg, 1992.
M. Amend, C. Jakobeit, L. Greiner, Verdauungskrankheiten 13 (1995), No. 1, p. 21.
K. Ewe, Therapiewoche 41 (1991), p. 77.
Y. Benmair, B. Fischel, E.H. Frei, T. Gilat, The American Journal of Gastroenterology 68 (1977), p. 470.
L. Trahms, R. Stehr, J. Wedemeyer, W. Weitschies, Biomedizinische Technik 35 (1990), p. 158.
K. Fitzgerald, IEEE Spectrum 27 (1990), p. 52.
W. Weitschies, J. Wedemeyer, R. Stehr, L. Trahms, IEEE Trans. Biomed. Eng. 41 (1994), p. 192.
New Methods for Determining the gastro–intestinal transit time, vol. 35 copy 7–8/1990, pp. 179–180, XP 000168176.

* cited by examiner

*Primary Examiner*—Gary E. Hollinden
(74) *Attorney, Agent, or Firm*—Jordan and Hamburg LLP

(57) ABSTRACT

The invention provides a marker whose position in a cavity inside of a living organism can be determined, in particular for detecting local passage speeds of the marker through the gastro-intestinal tract, preferably in the small intestinal tract. The object of the invention is to provide a marker whose magnetization can be reversed with relatively low field intensities. To that end, the marker consists of a first substantially spherical part which contains a magnetizable material and is surrounded on all sides by a second part which is provided with a substantially spherical receptacle adapted to the surface shape of the first part, the receptacle being filled with a low-viscosity fluid.

16 Claims, 2 Drawing Sheets

MARKER FOR DETERMINING ITS POSITION IN A CAVITY INSIDE THE ORGANISM OF A LIVING BEING

This application is a 371 of PCT/EP98/00940 filed Feb. 19, 1988.

BACKGROUND OF THE INVENTION

The invention relates to a marker, the position of which in a cavity inside a living organism is to be determined, in particular for determining local passage speeds of the marker while passing through a gastro-intestinal tract, preferably, a small bowel area. The marker is particularly adapted for use in a method and apparatus according to WO 97/09640.

There are medical examinations known which require repeated detection of local passage speeds of a marker while passing through the gastro-intestinal tract. This is the case, for example, with chronic inflammatory intestinal diseases such as Morbus Chron, functional gastro-intestinal diseases, and in physiological examinations of the gastro-intestinal tract. Conventional diagnosis techniques, such as X-ray examination under use of contrast meals, may not be utilized in the cases mentioned due to the radiation exposure. The same comes true for scintigraphic methods.

Known techniques which avoid radiation exposure are nuclear spin tomography [M. Reiser, W. Semmler (editor) "Magnetoresonanztomograhpie", Springer press, Berlin/Heidelberg, 1992], the sonography [M. Amend, C. Jakobeit, L. Greiner, Verdauungskrankheiten 13 (1995), No. 1, pg. 21], use of metal detectors [K. Ewe, Therapiewoche 41 (1991), pg. 77], inductive detection of soft magnetic tracers [Y. Benmair, B. Fischel, E. H. Frei, T. Gilat, The American Journal of Gastroenterology 68 (1977), pg. 170], and local position detection of permanent magnetic markers [L. Trahms, R. Stehr, J. Wedemeyer, W. Weitschies, Biomedizinische Technik 35 (1990), pg. 158].

Nuclear spin tomography, or magneto-resonance, is an expensive method which is not suitable for examinations which have to be repeated very often, and too slow for the detection of local passage speeds, which require time intervals in an order of size of 10 s for the successive position detection of markers [K. Fitzgerald, IEEE Spectrum 27 (1990), pg. 52].

Sonographic examinations have not been employed for the detection of local passage speeds up to now, but only for measuring general transit times of larger sections of the gastro-intestinal tract [M. Amend, C. Jakobeit, L. Greiner, Verdauungskrankheiten 13 (1995), No. 1, pg. 21], since air volumes in the abdominal cavity cannot be penetrated by ultrasound and would result in an erroneous position detection of the marker. Such deficiencies could be reduced by completely filling the bowel with a liquid, however, a filled bowel is not suited for a diagnosis due to the changed peristalsis.

It is feasible to determine the position of metal particles by metal detectors. However, the lateral accuracy of the position detection decreases with the increasing distance from the body surface and is worse than 1 cm at a distance of <10 cm [K. Ewe, Therapiewoche 41 (1991), pg. 77]. Said paper does not report of the accuracy of these depth-measurements. Since the accuracy of depth-measurements is generally worse than the lateral accuracy, this method is insufficient for local passage speed measurements.

The accuracy of position detection obtained with an inductive measurement of a soft-magnetic tracer satisfies examinations of the gastric contents decrease per unit time of a soft-magnetic meal having an initial volume of more than 100 cm³ [Y. Benmair, B. Fischel, E. H. Frei, T. Gilat, The American Journal of Gastroenterology 68 (1977), pg. 170]. However, on the one hand, a measurement of the local passage-speed in the bowels is not feasible, since the large test meal volume uncontrollably distributes while passing the bowels. On the other hand, the test volume cannot be reduced substantially since, otherwise, the secondary magnetic field produced by the tracer, even when highly compensated, will become so small that it cannot be separated from the residual signal of a primary magnetic field applied during measurement.

Furthermore, it is known to magnetize permanent magnetic markers before being administered to a patient [W. Weitschies, J. Wedemeyer, R. Stehr, L. Trahms, IEEE Trans. Biomed. Eng. 41 (1994), pg. 192], [DE 39 40 260]. However, the detection of the position of the markers via their secondary magnetic field is considerably affected by interference fields (for example, by the magnetic field of the earth) so that the measurements have to be carried out in an extremely magnetically screened special chamber. Even then this method is not suited for detection of the local passage speed i the entire gastro-intestinal tract. Hence, position detection is only feasible i the stomach or in the large bowel, due to the transversal and rotational movements of the marker, and even in these ranges, where the retention time of the marker is comparatively high, the accuracy is insufficient.

In WO 97/09640 an arrangement for and method of determining the position of a magnetizable marker has been proposed, whereby the marker is adapted to comprise a semi-hard magnetic material of a coercive force within a range of from $10^4$ up to $10^5$ A/m, and is spherosymmetrically embodied. Furthermore, according to the specification mentioned, the marker is made of an isotropic magnetic material of a relative residual magnetism of preferably >0.8, wherein the marker is substantially made of $\gamma$-$Fe_2O_3$ and/or $Fe_3O_4$. A disadvantage of the marker embodiment proposed consists in that the primary magnetic field for the magnetic reversal of the marker is very considerable.

It is an object of the present invention to provide a marker which is designed to be captured by a magnetic coil arrangement, whereby the magnetizing of the marker is reversible by virtue of comparatively low field strengths at a change of a pulse-shaped current flow in the magnetic coil arrangement.

SUMMARY OF THE INVENTION

According to the invention a magnetizable marker is manufactured of two parts, a first part being a substantially spherical part which is adapted to receive a magnetizable material or body. The first part being received by a second part in such a manner that it floats permitting all around rotation in the second part. While passing through the gastro-intestinal tract, a position of the external second part is determined by forces which are executed by feed pulp, intestinal wall, and by the peristalsis. In contrast thereto, the orientation of the internal and substantially spherical first part is determined by the field, for example, the magnetic field of the earth, exerted on the magnet. The orientation can be adjusted at will by an externally applied field which is stronger than the magnetic field of the earth, or by an accidentally present laboratory magnetic field. To this end, already a magnetic field strength of about 80 A/m is sufficient, which very easily can be produced by current-carrying coils or permanent magnets outside of a patient's body.

In order to eliminate the external interfering fields in the case of use of the marker in an apparatus, for example, according to WO 97/09640, a magnetic moment of the first part is rotated into a desired orientation, for example, at right angles to a plane of the patient's back by applying an external field $H_{ext}$ for a short time. Then the applied field is turned off for a short time and directly following, as fast as possible, the marker field is measured by sensors. After this measurement, the field $H_{ext}$ is applied in the opposite direction for a short time and the above procedure is repeated. By difference formation of both measured marker fields, the entire interfering effects are eliminated which did not change remarkably between both measurements. The times which are required for the orientation in the externally applied magnetic field and for a reverse rotation in the direction of the field of the earth or of the laboratory depend on, inter alia, a residual magnetic moment of a first part and on the viscosity of a liquid in which the first part is embedded. A simple electronic circuit, which does not require anything more than conventional state of art knowledge, will suffice to measure the magnetic field of the marker within a period of a few tenths of seconds after turning off of the external magnetic field $H_{ext}$. In order that the first part is practically still in the oriented state during this measurement, a back-rotation time of $\Delta t_R$ of about 10 sec. or more will be sufficient. The orientation time $\Delta t_A$ should not exceed 1 sec. in order to keep low the power for orientation by $H_{ext}$. The recommended values $\Delta t_R$ and $\Delta t_A$ can be obtained, under use of permanent magnets on sale, when liquids are employed which exhibit nearly the viscosity of water or exceed the same by a factory 100. Furthermore, it lies within the scope of the invention to affect both times $\Delta t_R$ and $\Delta t_A$ by a respective shaping of surfaces of the first and/or the second part and by a variation of the space between the surfaces of the first and the second part.

BRIEF DESCRIPTION OF THE FIGURES

The invention will be explained hereinafter in more detail by virtue of the embodiments. There is shown in.

DETAILED DESCRIPTION

Figure 1:
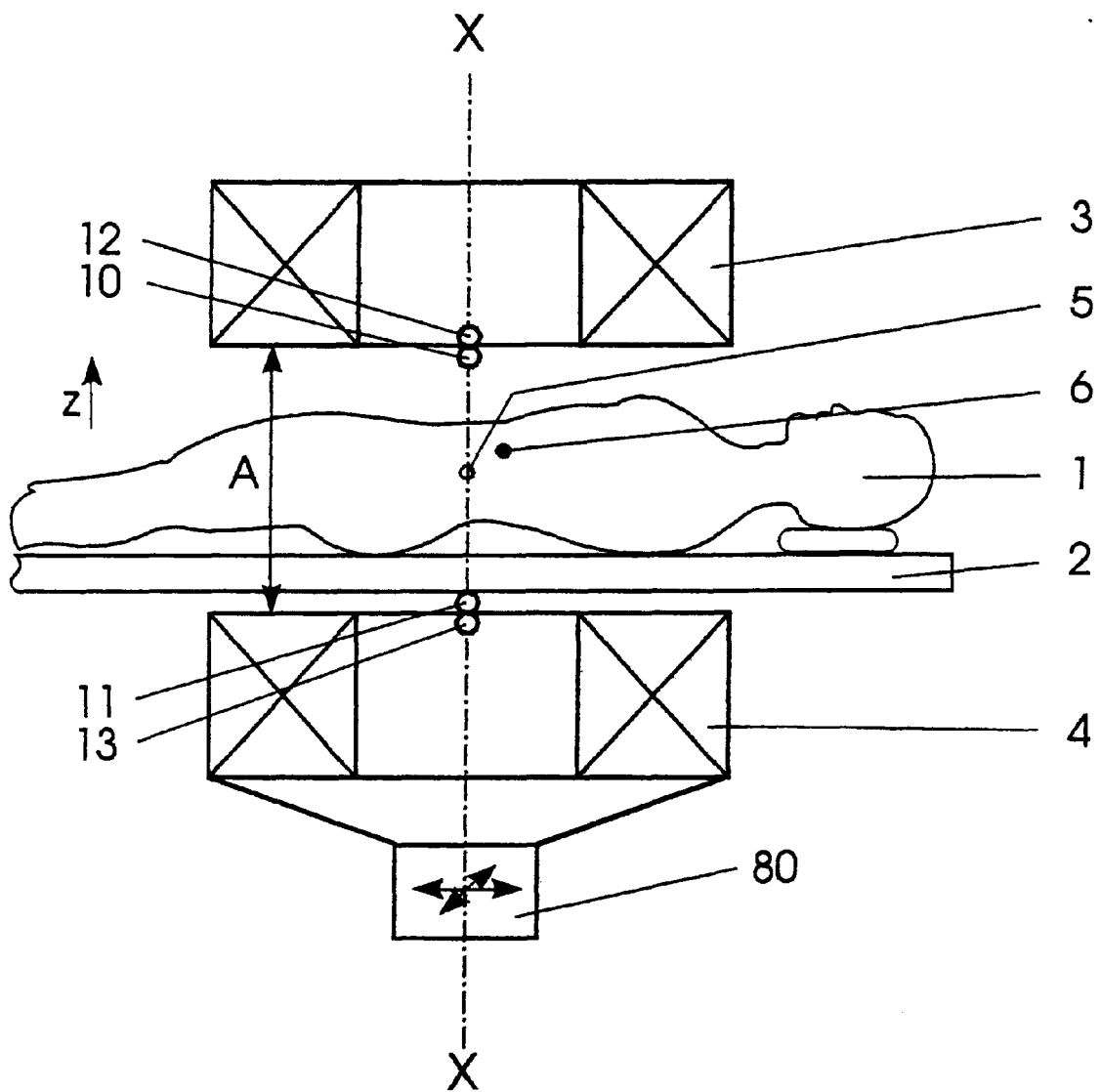
FIG. 1 the positioning of a patient in a feasible arrangement according to the prior art, FIG. 2 a section through a marker according to the present invention, FIG. 2a a section through a marker with a modified shape of the surface of the first part, and FIG. 2b a section through a marker being provided with two first parts.

In FIG. 1 a patient 1 whose gastro-intestinal tract has to be examined lies on a non-metallic non-magnetic table 2. Two identical coils 3 and 4 are arranged about a common axis X—X via their coil axes, spaced apart at an inside width A in an order of magnitude of about 30 cm. Current pulses produced by a pulse generator, not designated in more detail, are applied across the coils 3, 4. Thus, a maximum primary magnetic field is produced in a geometrical center 5 at, for example, time intervals of 1 s, depending on a current pulse frequency selected. A marker 6, described in more detail in FIG. 2, has orally been given to the patient 1.

Each of the coils 3, 4 is in a rigid connection with respective anisotropic magneto-resistive magnetic field sensors 10, 11, 12, 13. Thereby, the magnetic field sensors 10, 11 are conceived to exclusively detect a component $H_S^{\|}$ of a secondary magnetic field originating from the marker 6 which is in parallel to the axis X—X, whereas the magnetic field sensors 12, 13 are employed to detect a radial component $H_X^{\perp}$ of said secondary magnetic field which is at right angles to said axis. When the marker 6 is in the center of the common coil axis X—X, the magnetic field component $H_S^{\|}$, is detectable whereas the magnetic field component $H_S^{\perp}$ which is at right angles thereto, is zero. When the sensors of the magnetic field are activated and triggered in time intervals $t_1$, between two primary field pulses executed at time interval $t_2$, then the series connected radial sensors 12, 13 produce a pulse-shaped alternating voltage when the marker 6 is radially displaced by, for example, r=1 cm. The common coil axis X—X of the present example is now displaced by means for a relative positioning, which in its simplest form can be embodied by a cross-slide 80 connected to the coils 3 and 4, until the signal mentioned vanishes. When this occurs the coil axis X—X again is in the marker center. The relative position obtained is detected by a local sensor, not designated in more detail, and fed into a storage and evaluation unit.

After an axial displacement of the marker 6 off from the center 5 in z-direction, the two axial sensors 10, 11 produce pulse-shaped alternating voltages. These signals associated to the respective vertical marker position are also fed into the storage and evaluation unit, now shown. Hence, the required number of measuring values is provided for each actual marker position to uniquely describe the actual local position of the marker in the gastro-intestinal tract. The marker positions successively obtained in the way described, form a train of points which represents the path of the marker 6. The quotient of the space between adjacent points and the time interval between said points is a measure for the local passage speed of the marker 6 to be detected. The entire measuring data obtained can be displayed in three dimensions on a monitor subsequent to a respective evaluation and calibration operation during or after the examination of the marker passage in the patient.

Figure 2:
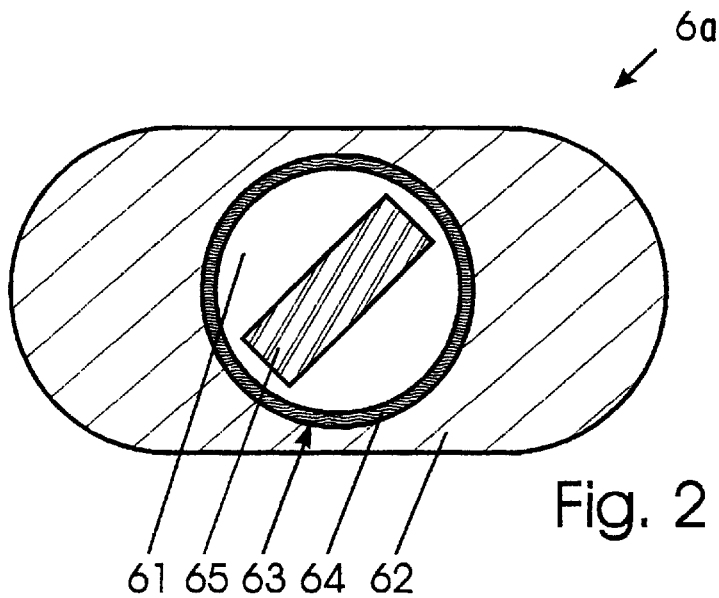

In FIG. 2 a first marker 62 is includes substantially spherical part 61, or core. Said part 61 is filled with a magnetizable material or contains a body 65 adapted to be magnetized. Furthermore, a second part 62, or shell, is provided comprising a receptacle 63 which, in the present example, is also given a spherical shape, adapted to a shape of a surface of said first part. Said receptacle 63 envelopes said first part 61 from all sides. The receptacle 63 is filled with a liquid 64 of low viscosity, enabling an all-around rotation of the first part 61 within the receptacle 63. The second part 62 can also be given a spherical external shape, however, with respect to the first kind of application of the marker 62 it is preferred to give the same an external shape similar to a capsule drug.

The advantage of a such embodied marker 62 consists in that the same can be magnetized in a strong field outside of the patient's body so that said first maker 62 becomes a source of a substantially stronger secondary magnetic field (about ten times stronger compared to a marker used in WO 97/09640) and, hence, produces greater sensor signals. The primary magnetic field produced according to FIG. 1 no longer has to reverse the magnetization of the marker, it only has to rotate part 61. To this end, a field suffices which, maximally, amounts to ten times the magnetic field strength of the earth, whereas one thousand times the magnetic field strength of the earth is required according to WO 97/09640. The coils provided for in WO 97/09640 can be designed considerably lighter and only need about 1% of the electric power required there.

Figure 2A:
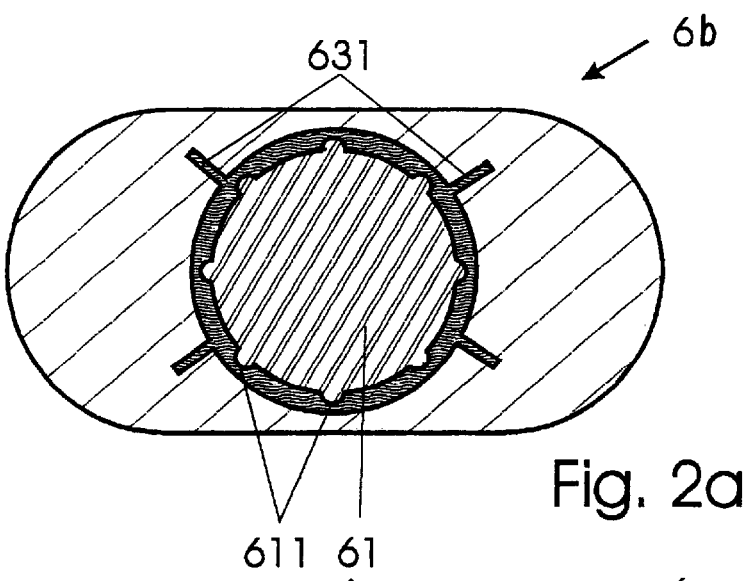

In FIG. 2a a sectional view of a second marker 6b is shown, in which the first part 61 is given a shape of surface provided with elevations 611. It also lies within the scope of the invention to provide the first part 61 with elevations 611 and/or with recesses (not shown in more detail), but also to provide the surface of the receptacle 63 with recesses 631, four of which are schematically indicated in FIG. 2a. In the case of the first part 61 being without elevations, the surface of the receptacle 63 can be provided with elevations. All the feasible embodiments disclosed up to here in connection with FIG. 2a are specifically designed to set and to default in the times for $\Delta t_R$ and $\Delta t_A$, due to a defined setting of the viscosity of the liquid 64, for example, by mixing of two components, in particular of oil, preferably of edible oil, and a specifically designed adaptation of the space between the surface of the first part 61 and the surface of the receptacle 63. Furthermore, it lies within the scope of the invention to fill the first part 61 completely with a magnetizable material, as indicated in FIG. 2a. It can also be advantageous to carry out the filling of the part 61 in such a manner that a center of mass of the part 61 lies outside of its geometrical center.

Figure 2B:
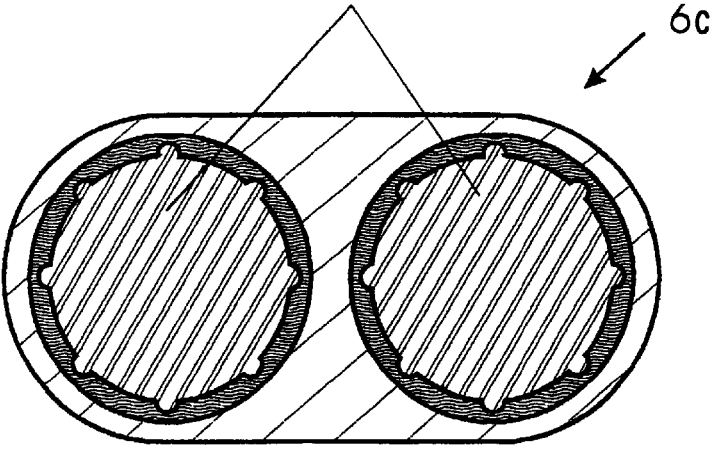

Finally, it also lies within the scope of the invention to provide for a plurality of first parts 61 within the second part 62 of a third marker 66, two of the same being represented in FIG. 2b. This leads, for example, to an increase of signals from the third marker 66.

All features disclosed in the specification, in the subsequent claims, and in the drawing are substantial for the invention both, individually and in any combination with one another.

What is claimed is:

1. A marker for determining a position thereof in a cavity inside a living organism, comprising:
    at least one first part which is substantially spherical and includes a magnetizable material;
    a second part defining a receptacle cavity which is substantially spherical conforming to a form of said at least one first part and having a larger volume than said at least one first part;
    said at least one first part being disposed in said receptacle cavity and thereby enveloped on all sides by said second part; and
    a liquid filling said receptacle cavity to envelope said at least one first part thereby permitting said at least one first part to freely rotate within said receptacle cavity.

2. The marker as claimed in claim 1, wherein said second part has an external shape with a form of a drug capsule.

3. The marker as claimed in claim 1, wherein a surface of said at least one first part is provided with at least one of elevations and recesses.

4. The marker as claimed in claim 1, wherein a surface of said receptacle cavity is provided with at least one of elevations and recesses.

5. A marker as claimed in claim 1 or 3, wherein said at least one first part has said magnetizable material disposed in such a manner that a center of mass of said at least one first part lies outside of a geometric center of said at least one first part.

6. A marker as claimed in claim 1, wherein the liquid is a mixture of two viscous components having differing viscosities thereby permitting adjustment of a viscosity of the liquid.

7. A marker as claimed in claim 1 or 6, wherein said liquid includes at least one oil.

8. A marker as claimed in claim 7, wherein at least one edible oil is employed as said at least one oil.

9. A method of tracing movement within a living organism, comprising the steps of:
    providing a marker including:
        a core part which is substantially spherical and includes a magnetizable material;
        a shell defining a receptacle cavity which is substantially spherical conforming to a form of said core part and having a larger volume than said core part;
        said core part being disposed in said receptacle cavity and thereby enveloped on all sides by said shell; and
        a liquid filling said receptacle cavity to envelope said core part thereby permitting said core part to freely rotate within said receptacle cavity;
    magnetizing said core part;
    administering said marker into the living organism;
    applying a magnetic field to the living organism to orient said core part within said marker; and
    determining positions of said marker within the living organism by detecting a magnetic field of the core part using detectors positioned relative to said living organism.

10. The method as claimed in claim 9, wherein said shell has an external shape with a form of a drug capsule.

11. The method as claimed in claim 9, wherein a surface of said core part is provided with at least one of elevations and recesses.

12. The method as claimed in claim 1, a surface of said receptacle cavity is provided with at least one of elevations and recesses.

13. A method as claimed in claim 9 or 11, wherein said core part has said magnetizable material disposed in such a manner that a center of mass of said core part lies outside of a geometric center of said core part.

14. A method as claimed in claim 9, wherein the liquid is a mixture of two viscous components having differing viscosities thereby permitting adjustment of a viscosity of the liquid.

15. A method as claimed in claim 9 or 14, wherein said liquid includes at least one oil.

16. A method as claimed in claim 15, wherein at least one edible oil is employed as said at least one oil.

* * * * *